(12) United States Patent
Kobayashi et al.

(10) Patent No.: US 8,086,016 B2
(45) Date of Patent: Dec. 27, 2011

(54) APPARATUS, A METHOD AND SOFTWARE FOR ANALYZING A CELL IMAGE

(75) Inventors: Tamiyo Kobayashi, Kunitachi (JP); Kosuke Takagi, Kawagoe (JP); Yuichiro Matsuo, Hachioji (JP)

(73) Assignee: Olympus Corporation, Tokyo (JP)

( * ) Notice: Subject to any disclaimer, the term of this patent is extended or adjusted under 35 U.S.C. 154(b) by 477 days.

(21) Appl. No.: 12/365,928

(22) Filed: Feb. 5, 2009

(65) Prior Publication Data

US 2009/0196482 A1    Aug. 6, 2009

(30) Foreign Application Priority Data

Feb. 5, 2008   (JP) .................................. 2008-025777

(51) Int. Cl.
  *G06K 9/00*   (2006.01)
(52) U.S. Cl. ........................................ 382/133; 382/128
(58) Field of Classification Search .......... 382/128–134; 128/920, 922

See application file for complete search history.

(56) References Cited

U.S. PATENT DOCUMENTS 5,891,646 A * 4/1999 Barak et al. ................ 435/7.2
7,279,338 B2 * 10/2007 Kim et al. .................. 436/177

FOREIGN PATENT DOCUMENTS

JP    2004-054347    2/2004

OTHER PUBLICATIONS

Hundle, Bhupinder et al., "Overexpression of ∈-Protein Kinase C Enhances Nerve Growth Factor-induced Phosphorylation of Mitogen-activated Protein Kinases and Neurite Outgrowth", The Journal of Biological Chemistry (1995), pp. 30134-30140, vol. 270, No. 50, the American Society for Biochemistry and Molecular Biology, Inc.

* cited by examiner

*Primary Examiner* — David Mis
(74) *Attorney, Agent, or Firm* — Scully, Scott, Murphy & Presser, P.C.

(57) ABSTRACT

A cell image analysis apparatus and method for judging, quickly and with good reproducibility, the presence or absence of a membrane translocation reaction occurring in a cell owing to application of an arbitrary stimulus to the cell using a fluorescence microscope. The inventive apparatus has: an element acquiring as an image data a fluorescence microscopic image of a cell after the application of the stimulus; an element determining a region occupied by the cell in the fluorescence image of the cell; an element determining a contour line of the cell having a width of a predetermined number of pixels from a periphery of the region occupied by the cell; and an element judging the presence or absence of the membrane translocation reaction based on a brightness value on the contour line of the cell and a brightness value in an inside of the contour line of the cell.

21 Claims, 4 Drawing Sheets

APPARATUS, A METHOD AND SOFTWARE FOR ANALYZING A CELL IMAGE

TECHNICAL FIELD

This invention relates to an apparatus and a method of an image analysis of a microscopic image of a cell obtained with an optical microscope, and software for them, and more particularly, to an apparatus, a method and software for analyzing a fluorescence microscopic image of a cell to judge the presence or absence of occurrence of a membrane translocation reaction observed in a cell.

BACKGROUND ART

It is known that, in various cells, chemical stimulation with a bioactive substance or a drug, or physical stimulation with light, electricity, mechanical force, etc, induces a phenomenon, called as "membrane translocation reaction", of accumulation of certain kinds of intracellular proteins onto a cell membrane. As well known in ones skilled in the art, when a membrane receptor, such as a G protein binding protein on a cell membrane (GPCR: G Protein Coupled Receptor), receives a specific substance (ligand) or a photon, etc. from the exterior, this becomes a trigger, i.e., a stimulus, making the reactions of various materials progress in series within a cell, whereby stimulus information is transmitted one after another within the cell. "Membrane translocation reaction" is a phenomenon as a part of such processes of the stimulus or signal information transmission in a cell, in which certain kinds of proteins having been liberated in cytoplasm or present in cellular organelles before the stimulation move to a cell membrane. Such a membrane translocation reaction in a cell is made observable directly under an optical microscope through labeling fluorescent dye, etc. on proteins or other biological molecules having a membrane translocation activity (producing a membrane translocation reaction), and thus, in the fields of cell biological, medical and pharmacological researches and drug designing, it has been tried to judge whether or not an arbitrary cell produces a membrane translocation reaction in response to an arbitrary material or stimulus under an optical microscope, thereby evaluating whether or not the arbitrary material or stimulus has a physiology activity (especially as an intracellular signal transmitter substance) to the arbitrary cell, or whether or not the arbitrary material or stimulus is effective as a new medicine or a treatment (Drug Discovery).

In the past, in the trial of observation of a membrane translocation reaction, the labeling of a specific protein having a membrane translocation activity in a living cell required a skilled technique, such as microinjection of fluorescently labeled proteins or biological molecules, etc. into individual cells, and also, in this case, the number of cells observable at once was small. However, through staining specific proteins in many cells at once with a fluorescent dye capable of being taken in a living cell and labeled to a specific material or through cultivating at once a large number of cells in which a protein fusing with a fluorescent protein, such as GFP, is expressed through gene introduction technique, it is becoming possible to observe motions of intracellular proteins in many cells by using the fluorescent dye or fluorescent protein as a label. For instance, as described in non-patent document 1, it has been carried out for adhesive cells Hela (cervical cancer cells), etc., to prepare a large quantity of the cells in which GFP-fused protein of protein kinase C (PKC), membrane-translocation-active protein, is made expressed through gene introduction technique, and to observe and judge, under a fluorescence microscope, whether or not a membrane translocation reaction occurs when a membrane translocation signal PMA or other active drug is applied to many cells expressing GFP-fused PKC (It is known that PKC, which has been liberated in cytoplasm before stimulation, binds to the inside of a cell membrane when the cell receives a stimulus of PMA, etc.). According to such an experiment, it becomes possible to observe and evaluate a cellular responsiveness to a certain stimulus for many cells at once, and thus, it is very advantageous for the search of an intracellular signal transmitter substance and the screening of arbitrary substances having a physiological activity.

PRIOR ART DOCUMENT

Patent document 1: Patent Laid-Open publication 2004-54347
Non-patent document 1: The Journal of Biological Chemistry, Vol. 270, No. 50, 1995, p. 30134-30140

SUMMARY OF INVENTION

In the judging of the presence or absence of a membrane translocation reaction with a fluorescence microscope, a fluorescence microscopic image (hereafter, referred to as a "fluorescence image".) of a cell obtained through the objective is observed by eye or by photographing the fluorescence image with a camera attached to the microscope. Then, in reliance upon the judgment of an observer or an experimenter, for each individual cell, it is judged that the membrane translocation reaction has occurred if the fluorescence intensity on a cellular periphery relatively increases after stimulation. In a case that a fluorescence image captured with a camera can be taken into an arbitrary image processing device, etc. (for example, refer to the patent documents 1), since the internal and external fluorescence intensity distribution of a cell can be represented in a graph form, one can also judge whether or not proteins have accumulated near a cell membrane from the change of the fluorescence intensity of a cellular periphery by looking at the graph of the fluorescence intensity distribution for each cell, instead of the fluorescence image itself. Further, in the screening of physiology activities of arbitrary substances, the number of cells having produced the membrane translocation reaction is counted, and the result of the number of counts is used for the evaluation of an activity of a substance.

However, in the judgment as described above, determining whether or not it is admitted that the fluorescence intensity on a cellular periphery has increased owing to a stimulus in a certain cell, namely, whether or not a membrane translocation reaction occurred, is finally left to a judgment of an observer, and therefore, the variation in the judgments may arise. Actually, in the living cells, the degree of the change of the fluorescence intensity owing to a membrane translocation reaction vary depending upon each individual cell, e.g. a cellular shape, a cellular thickness (in the direction of an optical axis of an optical microscope), and so, if a judgment of the presence or absence of a membrane translocation reaction is dependent upon an observer, the criterion for the judgment may vary at every time and/or every observer, and accordingly, the objectivity or reproducibility in the judgment results can be not so high. Further, although no enormous labor would be required in judging the presence or absence of a membrane translocation reaction for one cell by means of the graph of fluorescence intensity distribution, the judging one by one for the increased number of cells requires much time and much burden. Also, the variation in the judgments of an observer would induce errors in the count result of the cells producing a membrane translocation reaction when the total number of cells becomes large, which reduces the reliability of the evaluation result for the activity in the screening of physiological activities of arbitrary substances, etc.

Thus, if the judgment of the presence or absence of a membrane translocation reaction can be carried out without requiring the dependence on the individual judgments for individual cells by an observer or an experimenter, reliable results will be expected to be obtained without long time or heavy burden even when the number of cells to be judged increases.

Accordingly, one object of the present invention is to provide a cell image analysis apparatus or method for judging the presence or absence of a membrane translocation reaction owing to an arbitrary stimulus in an arbitrary cell using a fluorescence microscope, where the judgment of the membrane translocation reaction of an individual cell is carried out without being influenced by the variation in judgments of an observer or an experimenter.

Moreover, another object of the present invention is to provide an apparatus or a method as described above, where the judgment of the presence or absence of a membrane translocation reaction can be performed quickly even when the number of cells to be judged increases. In this regard, in such an apparatus or a method, it will be more preferable that from the acquisition of a fluorescence image of a cell to the judgment of the presence or absence of a membrane translocation reaction can be automatically performed after setting a cell sample to an optical microscope.

Furthermore, one further object of the present invention is to provide software which realizes a cell image analysis apparatus or method as described above.

According to the present invention, there are provided a novel cell image analysis apparatus, a novel computer program and a novel method for cell image analysis, where the presence or absence of a membrane translocation reaction occurring in a cell owing to an arbitrary stimulation to the cell is judged irrespectively of the variation in judgments of an observer or an experimenter.

The inventive cell image analysis apparatus is characterized by comprising a means that acquires, as an image data, a fluorescence microscopic image of a cell after stimulation in which cell translocation molecules moving to a cell membrane in a membrane translocation reaction are fluorescently labeled; a means that determines a region occupied by the cell in the image data of the fluorescence microscopic image of the cell; a means that determines a contour line of the cell having a width of a predetermined number of pixels from a periphery of the region occupied by the cell; and a means that judges a presence or an absence of a membrane translocation reaction based on a brightness value on the contour line of the cell and a brightness value in an inside of the contour line of the cell in the image data of the fluorescence microscopic image of the cell.

According to the above-mentioned inventive structure, first, a fluorescence microscopic image (fluorescence image) of a cell whose translocation molecules moving to a cell membrane in a membrane translocation reaction are fluorescently labeled is acquired after stimulation as an image data in a usual manner. Since the image data of the fluorescence image is an assembly of pixels having a brightness value and a coordinate, the fluorescence intensity of a coordinate in a fluorescence image will be known when the coordinate is specified. Then, in the inventive apparatus, a region occupied by a cell in the image data of the fluorescence image is determined based on the fluorescence intensity associated with a coordinate in the acquired fluorescence image, and a contour line having the width of a predetermined number of pixels from the periphery of the region occupied by the cell in the image of the cell is determined. And, the judgment of the presence or absence of a membrane translocation reaction is carried out based on the brightness value on the contour line of the cell and the brightness value in the inside of the contour line of the cell in the image data of the fluorescence microscopic image of the cell. In this case, preferably, the average of the brightness values of all the pixels on the contour line of the cell and the average of the brightness values of pixels in the inside of the contour line of the cell are computed, and when the ratio of the average on the contour line of the cell to the average in the inside of the contour line of the cell exceeds a predetermined value, it may be judged that a membrane translocation reaction occurred.

According to this structure, the judgment of a membrane translocation reaction is carried out without being influenced by a subjective judgment of an observer or an experimenter, and thereby, the reliability of the judgment result will increase. Moreover, since the operation of the above-mentioned apparatus can be automated through the image processing technique, it becomes unnecessary for an observer or an experimenter to make a judgment of a membrane translocation reaction in each measurement, which enables the reduction of the time and burden required for a judgment of a membrane translocation reaction.

In the above-mentioned structure, the fluorescence microscopic image may include fluorescence microscopic images of a plurality of cells (namely, a plurality of cells may be included in one image data), and in that case, the means that determines a region occupied by a cell may determine a region occupied by each of the plurality of cells; the means that determines a contour line of a cell may determine a contour line of each of the plurality of cells; and the means that judges a presence or an absence of a membrane translocation reaction may judge the presence or absence of a membrane translocation reaction based on the brightness value on the contour line and the brightness value in the inside of the contour line for each of the plurality of cells. Since this structure is also made with the automatic computation processing using the coordinates and brightness values of the pixels in the image data, an observer or an experimenter will not make a judgment of a membrane translocation reaction for each cell, whereby the time and burden required for the judgments of a membrane translocation reaction will be largely reduced even if the number of cells to be observed at once increases. Moreover, since the criterion of the judgment of a membrane translocation reaction is relied not on the feeling of an observer or an experimenter but on the brightness values on the individual contour lines of cells and the brightness values in the insides of the respective contour lines, no variation in the criterion depending upon individual cells occurs, and thereby the objectivity and reproducibility of the judgment results are improved.

As already noted, the judgment of a membrane translocation reaction is often used for the evaluation of a physiological activity of an arbitrary substance. In that case, how many cells produce a membrane translocation reaction in response to a certain stimulus becomes a standard for a physiological activity. Thus, in the inventive apparatus, the means that determines a region occupied by a cell may have a means that counts the number of a plurality of cells in a fluorescence microscopic image. In that case, an observer or an experimenter will be saved the burden for manually counting the number of cells in the image data. Moreover, since the evaluation of a physiological activity is often conducted based upon the ratio of the number of cells producing a membrane translocation reaction to the total number of cells applied with the stimulus, the apparatus may be designed to automatically compute the ratio of the number of cells producing a membrane translocation reaction.

Further, the above-mentioned inventive apparatus may be used in the judgment of a membrane translocation reaction for an arbitrary cell. In that case, the amount of proteins having accumulated on a cell membrane or the manner of the appearance of the accumulation condition of proteins in a fluorescence image will vary depending upon the kind of a cell or an experimental condition, and thus, the way of the spreading of the fluorescence intensity around a cell membrane at the occurrence of a membrane translocation reaction will also vary. Under such a condition, if the width of a contour line is too wider or too narrower than the width of the region where proteins having accumulated around a cell membrane are distributed, in both the cases, the difference in the intensity between when a membrane translocation reaction has occurred and when no membrane translocation reaction has occurred would decrease, so that the change of the fluorescence intensity around the cell membrane owing to a membrane translocation reaction could not be acceptably captured. Then, in the above-mentioned inventive apparatus, the predetermined width of a contour line to be determined in the means that determines a cellular contour line can be set up by a user.

Further, in the above-mentioned inventive apparatus, as understood from the above, the judgment of a membrane translocation reaction is dependent on the width and brightness value of a cellular contour line, and so, if the position of the focus of an objective relative to a cell is shifted out, a region occupied by the cell in a fluorescence image or the spreading way and intensity of the light around a cell membrane will vary, which would induce an error in the criterion of a membrane translocation reaction, and accordingly, it is preferable that the position of the focus of the objective relative to a cell is always fixed. However, in an actual measurement, the height and/or position of an objective of a fluorescence microscope can be moved out during the capturing of a fluorescence image, or the relative position of the upper surface or bottom surface of an observation sample container to the focus of an objective can vary during the moving of the field of view of the objective (in practical, the position of the observation sample is moved). Thus, in the inventive apparatus, when a cell adheres on the bottom or upper surface of an observation sample container, there may be provided a means that controls the position of an objective to set the focus of the objective to the cell by automatically adjusting the focus of the objective of the fluorescence microscope to the bottom or upper surface of the observation sample. Thereby, when the fluorescence microscope used with the inventive apparatus is equipped with the function that automatically controls the position of an objective, an observer or an experimenter can stably obtain a fluorescence image of a cell without checking the position of the objective, and thus, the judgment of a membrane translocation reaction based on the brightness value on a cellular contour line can be carried out stably (without variation).

By the way, the functions of the above-mentioned inventive apparatus may be performed in an arbitrary computer. Thus, according to another aspect of the present invention, there is provided a computer program for cell image analysis that judges the presence or absence of a membrane translocation reaction occurring in a cell owing to an application of an arbitrary stimulus to the cell, characterized in that the computer program makes a computer execute procedures of:

acquiring, as an image data, a fluorescence microscopic image of a cell after stimulation in which cell translocation molecules moving to a cell membrane in a membrane translocation reaction are fluorescently labeled; determining a region occupied by the cell in the image data of the fluorescence microscopic image of the cell; determining a contour line of the cell having a width of a predetermined number of pixels from a periphery of the region occupied by the cell; and judging the presence- or absence of the membrane translocation reaction based on a brightness value on the contour line of the cell and a brightness value in the inside of the contour line of the cell in the image data of the fluorescence microscopic image of the cell.

Similarly to the inventive apparatus, the above-mentioned inventive computer program may be designed to compute an average of brightness values of all pixels on the contour line of the cell and an average of brightness values of pixels in the inside of the contour line of the cell and to judge that the membrane translocation reaction occurred when a ratio of the average on the contour line of the cell to the average in the inside of the contour line of the cell exceeds a predetermined value in the procedure of judging the presence or absence of the membrane translocation reaction. Also, in a case that the fluorescence microscopic image includes fluorescence microscopic images of a plurality of cells, the inventive computer program may be designed to determine a region occupied by each of the plurality of cells in the procedure of determining the region occupied by the cell; to determine a contour line of each of the plurality of cells in the procedure of determining the contour line of the cell; and to judge the presence or absence of a membrane translocation reaction based on a brightness value on the contour line of the cell and a brightness value in the inside of the contour line for each of the plurality of cells in the procedure of judging the presence or absence of the membrane translocation reaction. In this case, it may be designed to count the number of the cells in the fluorescence microscopic image and to compute a ratio of the number of cells producing the membrane translocation reaction in the cells in the fluorescence microscopic image.

Moreover, the feature in the inventive apparatus) namely, the structure wherein a region occupied by a cell and its contour line are determined from a fluorescence image of the cell acquired as an image data, and then the presence or absence of a membrane translocation reaction is judged based on a brightness value on the cellular contour line and a brightness value in the inside of the cellular contour line in the image data of the fluorescence microscopic image of the cell, can be realized in a method of judging a presence or an absence of a membrane translocation reaction occurring in a cell owing to an application of an arbitrary stimulus to the cell. Thus, according to one more aspect of the present invention, there is provided a method for judging a presence or an absence of a membrane translocation reaction, characterized by comprising steps of: acquiring, as an image data, a fluorescence microscopic image of a cell after stimulation in which cell translocation molecules moving to a cell membrane in a membrane translocation reaction are fluorescently labeled; determining a region occupied by the cell in the image data of the fluorescence microscopic image of the cell; determining a contour line of the cell having a width of a predetermined number of pixels from a periphery of the region occupied by the cell; and judging the presence or absence of the membrane translocation reaction based on a brightness value on the contour line of the cell and a brightness value in the inside of the contour line of the cell in the image data of the fluorescence microscopic image of the cell. According to this method, it becomes possible to judge the presence or absence of a membrane translocation reaction stably and quickly without being influenced by subjective or sensuous judgment criterion of an observer or an experimenter.

In this method, similarly to the inventive apparatus, in the step of judging the presence or absence of the membrane translocation reaction, it may be conducted to compute an average of brightness values of all pixels on the contour line of the cell and an average of brightness values of pixels in the inside of the contour line of the cell and to judge that the membrane translocation reaction occurred when a ratio of the average on the contour line of the cell to the average in the inside of the contour line of the cell exceeds a predetermined value. Also, in a case that the fluorescence microscopic image includes fluorescence microscopic images of a plurality of cells, it may be conducted to determine a region occupied by each of the plurality of cells in the step of determining the region occupied by the cell; to determine a contour line of each of the plurality of cells in the step of determining the contour line of the cell; and to judge the presence or absence of the membrane translocation reaction based on the brightness value on the contour line of the cells and the brightness value in the inside of the contour line for each of the plurality of cells in the step of judging the presence or absence of the membrane translocation reaction, and also, it may be conducted to count the number of the cells in the fluorescence microscopic image and/or to compute a ratio of the number of cells producing the membrane translocation reaction in the cells in the fluorescence microscopic image.

In the above-mentioned present invention, as one example, the membrane translocation reaction to be judged is a reaction that proteins which have been liberated into cytoplasm of a cell accumulate onto a cell membrane of the cell in response to stimulation to the cell. Further, according to the present invention, it can also be judged that the presence or absence of occurrence of a reaction that proteins present in an organelle in a cell accumulate onto a cell membrane of the cell in response to stimulation to the cell. Preferably, the cell is an adhesive cell to which the focus of an objective is easily adjusted.

Cells whose translocation molecules moving to a cell membrane in a membrane translocation reaction are fluorescently labeled may be prepared, for example, by introducing, into cells, a gene for expressing the translocation molecules while fusing with a fluorescent protein, and then making the translocation molecules fusing with the fluorescent protein express in the cell prior to the acquiring of a fluorescence microscopic image of the cell, or by introducing, into cells, a gene for introducing a tag molecule into the translocation molecules; making the translocation molecules with the introduced tag molecules express in the cell; and then introducing a fluorescent dye capable of binding specifically to the tag molecules into the cell so as to fluorescently label the translocation molecules prior to the acquiring of a fluorescence microscopic image of the cell. Of course, the translocation molecules may be fluorescently labeled by a method other than the above-mentioned method, and such a case belongs to the scope of the present invention.

As understood from the above-mentioned inventive structures, in accordance with the inventive apparatus, program or method, since the sensuous judgment of a membrane translocation reaction for an individual cell from a fluorescence image by an observer or an experimenter is not conducted, the judgment result will be free of variation of the judgments depending upon observers or experimenters, and therefore the objectivity and reproducibility are improved. Moreover, as explained in conjunction with the structures of the inventive apparatus, because the judgment of an membrane translocation reaction of the present invention can be carried out automatically through computation processing by using the image data obtained through the digitization of a fluorescence image of a cell, the labor or time required for the judgments is reduced, and even when the number of cells to be judged increases, the judgment results will be obtained quickly.

It should be understood that the inventive apparatus, program or method can also be advantageously used for evaluating gene introduction efficiency. In the case of the evaluation of gene introduction efficiency, for instance, it is tried to introduce a gene for fluorescently labeling a protein related to a membrane translocation reaction or a protein having a translocation characteristic into a cell by a gene introduction technique to be evaluated. If the gene introduction technique is successful, a fluorescently labeled protein will be expressed, and a membrane translocation reaction in response to a predetermined stimulation will be observed. And, the gene introduction efficiency is determined by the reaction ratio of the membrane translocation reaction. In such a case, it is required to judge whether or not the membrane translocation reaction occurred for a lot of cells, but, in accordance with the present invention, even in such a case, it is expected that the evaluation result can be provided quickly and reliably.

Other objects and advantages of the present invention will become clear in the explanation of the following preferable embodiments of the present invention.

BRIEF EXPLANATION OF THE DRAWINGS

In FIG. 2B, the reason for the low fluorescence intensity in the center of the cell is because the fluorescently labeled proteins are not distributed in a nucleus. In FIGS. 2C and 2D, since the fluorescently labeled proteins in cytoplasm move to the cell membrane, the contrast between the cytoplasm and the nucleus becomes almost lost.

BEST MODE FOR CARRYING OUT THE INVENTION

In the followings, the present invention is explained in detail about some preferable embodiments, referring to the attached drawings.

Structure of a Fluorescence Microscope Observation System

Figure 1:
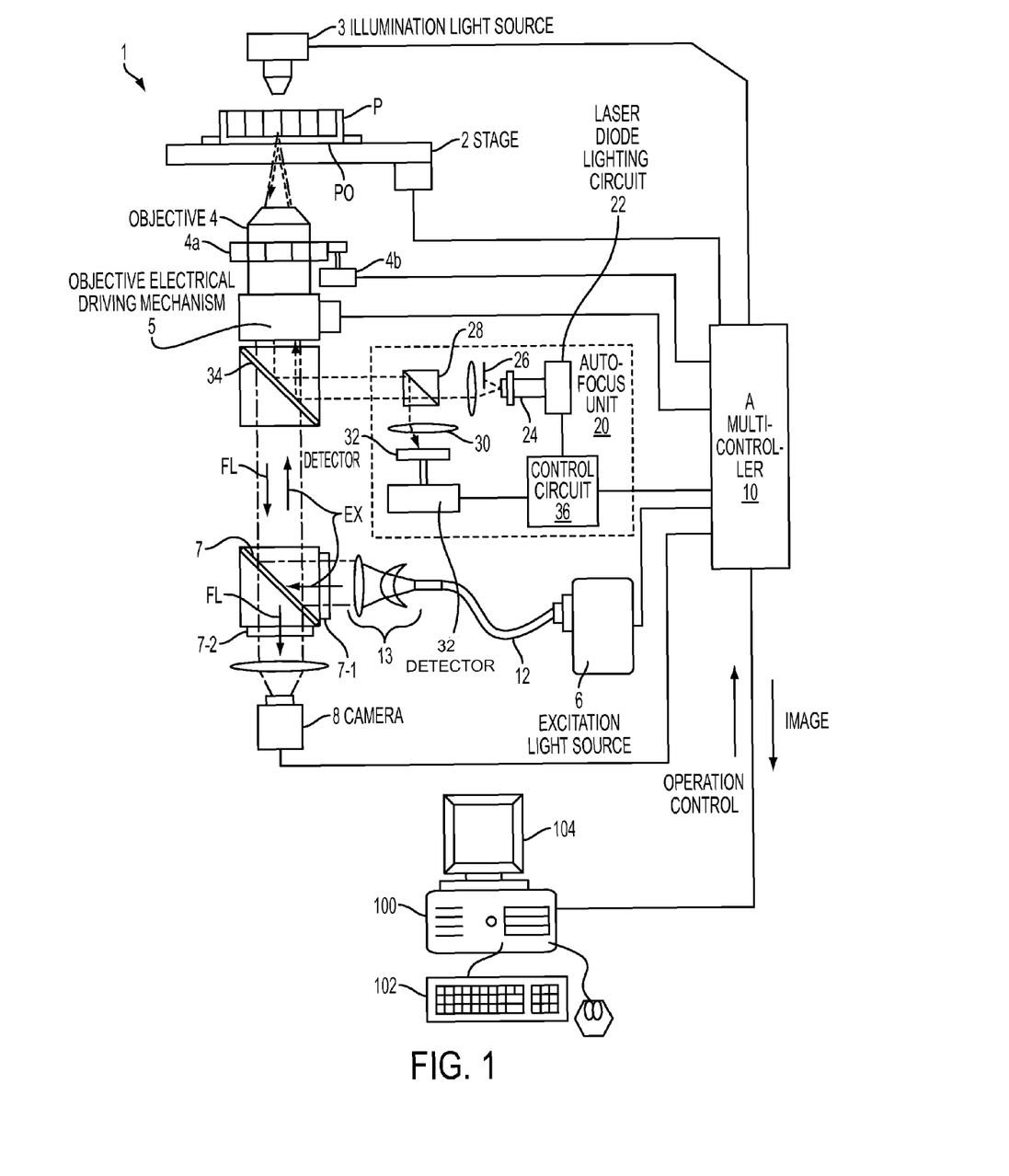
FIG. 1 is a schematic diagram of a fluorescence microscope system incorporating a preferable embodiment of a cell image analysis apparatus of the present invention.

FIG. 1 schematically represents a fluorescence microscope observation system incorporating a preferable embodiment of a cell image analysis apparatus for the judging of a membrane translocation reaction of a cell in accordance with the present invention. In the drawing, portions, not relevant to the structures of the present invention, are omitted for the simplification of the explanation.

Referring to the drawing, the fluorescence microscope observation system includes an inverted type fluorescence microscope 1 and an image analysis apparatus 100. Similarly to normal fluorescence microscopes, the fluorescence microscope 1 comprises a stage 2 electrically movable in the XY directions (horizontal) on which stage a cell sample P (for example, plastic micro titer plate having 24 wells) is laid; an illumination light source 3 for transmitted light observation; an objective 4; an objective electrical driving mechanism 5 which adjusts the position (height) of the objective; an excitation light source 6 for fluorescence observation; a dichroic mirror 7; a camera 8 for capturing a fluorescence image of a cell; and a multi-controller 10 which performs operational control of each of the above-mentioned parts of the fluorescence microscope 1 while cooperating with an image analysis apparatus 100. When a fluorescence observation is performed in the fluorescence microscope 1, the excitation light EX from the excitation light source 6 reflects on the dichroic mirror 7, passes through the objective 4, and illuminates the cell sample P, and the fluorescence EFL from the fluorescent labels in cells excited by the excitation light passes through the objective 4, penetrates the dichroic mirror 7, and forms an image on the light receiving surface (not shown) of the camera 16. In the dichroic mirror 7, as well known in persons skilled in the art, a filter 7-1 for excitation and a filter 7-2 for fluorescence (or for receiving light) are set such that the cell sample is excited with the light of a specific wavelength, and only the fluorescence from the sample enters into the light receiving surface of the camera. Further, since the optical system of the illustrated optical microscope is so-called "Infinite system", an image-formation lens is put in front of the camera such that the image of the focal plane of the objective 4 will be formed on the light receiving surface. And, the camera may be a video camera usually used in this field, such as a CCD or a cooled CCD. The excitation light source 6 may be a well-known arbitrary light source in this field, such as a mercury lamp, a xenon lamp, and a laser. In the illustrated example, LEDs of the emission wavelength of R (620 nm), G (520 nm), B (460 nm), and UV (365 nm) are built-in, and it is designed that the lights of LEDs are combined and introduced to one optical fiber 12 and the emitting light of the optical fiber is made into a parallel beam with the lens set 13, and led to the dichroic mirror 7.

The objective 4 attached to the fluorescence microscope 1 may be of an arbitrary magnification. In the present invention, the whole of a cell or a plurality of cells of ten and several μm to several tens μm are observed at once and taken into the analysis apparatus as image data, and thus, typically, an objective having a magnification of 40 (dry type) is used. In such an objective, usually, there is provided a compensation ring 4a which adjusts the focal position of the objective according to the thickness of a cover glass (or slide glass) P0 on the side of the cell sample P facing to the tip of the objective. Preferably, this compensation ring 4a may be operated with a stepping motor 4b in an arbitrarily provided apparatus to adjust the focal position of the objective automatically.

Furthermore, it is preferable that the illustrated fluorescence microscope 1 is provided with an autofocus unit (automatic focus adjusting mechanism) 20 which drives and controls the objective electrical driving mechanism 5 to automatically set the focal position of the objective 4 to the surface where the cells in the cell sample P are present. As explained later, in the analysis of cell images of the present invention, the fluorescence intensity on a contour line of a predetermined width defined along with the periphery of cells is referred to, where, if the focal position of the objective is moved out during a measurement, the position and intensity of the contour line defined in the image data would vary and this variation might affect the judgment result of a membrane translocation reaction. Then, in order to avoid the occurrence of this inconvenience, the autofocus unit is provided so that the focal position of the objective can be maintained at a fixed height in the cell sample P.

The illustrated autofocus unit 20 is of so called a "pupil splitting type laser autofocus unit", in which the position of the objective 4 relative to the bottom surface of the cell sample P is adjusted automatically by means of the reflected light of laser light applied to the bottom surface of the cell sample P through the objective 4. Briefly explaining its mechanism, first, the laser light of infrared light with a wavelength of 785 nm (dotted lines with arrows in the drawing), emitted from a laser diode 24 energized by a laser diode lighting circuit 22, passes through a diaphragm 26 and a beam splitter 28; reflects on a dichroic mirror for autofocus 34 (light with a wavelength of 700 nm or more is reflected) equipped in the optical path in the fluorescence microscope 1; enters into the objective 4 and reaches to the cover glass on the bottom surface of the cell sample P. At least a part of the laser light having reached to the cover glass reflects thereon, and, passes through the objective 4 again; reflects on the dichroic mirror 34 for autofocus; and further reflects on a beam splitter 28 in this time; and is received with a detector 32 through a condenser lens 30. In the optical system of this structure, the incidence position of the laser light into the objective 4 is rendered eccentric relative to the center axis of the objective, and thereby the position of the spot of the laser light which reflects on the bottom surface of the cell sample P; passes through the objective 4 again; and is received on the detector 32, will vary depending on the interval between the objective 4 and the bottom surface of the cell sample P. Thus, while the position of the spot of the laser light on the detector 32 is previously defined when the focus of the objective 4 is in agreement with the bottom surface of the cell sample P, the objective electrical driving mechanism 5 is controlled so that the position of the laser light on the detector 32 will be maintained in the previously defined position during the capturing of a fluorescence image of a cell. This control is automatically executed by an AF control circuit 36 based on the information on the position of the laser spot from the detector 32, and thus, by setting up previously the interval between the objective 4 and the bottom surface of the cell sample P, then, it will become unnecessary for an observer or an experimenter to adjust the focus of the objective. The AF control circuit 36 may also be designed to control the emission power or ON/OFF of the laser diode 24 through the laser diode lighting circuit 22.

In this connection, this autofocus unit 20 is not an indispensable structure in the present invention, and thus, in a case that this mechanism is not equipped on the microscope 1, an observer or an experimenter may adjust the focal position of the objective 4 in manual operation, and such a case also belongs to the scope of the present invention. Further, an automatic focus adjusting mechanism other than the illustrated example may be employed.

The multi-controller 10 controls the operations of the illumination light source 3 for transmitted light observation, the electric stage 2, the camera 16, and the autofocus unit 20 (objective electrical driving mechanism 5) based on the instructions from the image analysis apparatus 100, and also transmits fluorescence images of cell samples captured with the camera 16 to the image analysis apparatus 100. The structure of the multi-controller 10 may be designed in an arbitrary manner well-known for a person skilled in the art. The communication between the multi-controller 10 and image analysis apparatus 100 may be conducted in an arbitrary type, such as CAN communication, or USB connection.

Each of the means in the inventive cell image analysis apparatus, each procedure in the inventive program and each processing step in the inventive method are realized with the structures and operations of the image analysis apparatus 100. The image analysis apparatus 100 may be constituted by a computer capable of executing various kinds of arbitrary image processings well-known for a person skilled in the art. The image analysis apparatus 100, when operated, executes the inventive programs, memorized in the built-in storage medium, for the judging of a membrane translocation reaction in the manner explained in detail below. The image analysis apparatus 100 is provided with a keyboard 102 into which instructions of an observer or an experimenter are inputted; and a monitor 104 on which the operational condition of each part of the fluorescence microscope system and a fluorescence image of the cell sample captured with the camera 16 are displayed in manners similar to usual personal computers. In this regard, although the multi-controller 10 and the image analysis apparatus 100 are constituted as different units in the illustration, the multi-controller 10 may be one unit with the image analysis apparatus 100. Further, although the image analysis apparatus 100 may be a personal computer for general purposes, it may be constituted as a unit or an apparatus specialized for the cell image analysis in accordance with the present invention.

The Principle of a judgment of a Membrane Translocation Reaction

Figure 2A:
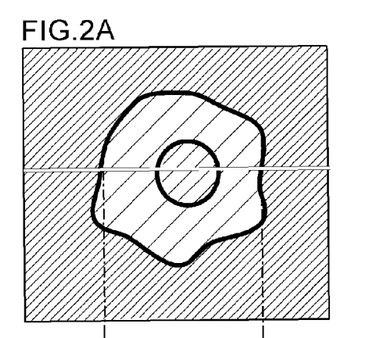
FIG. 2A is a schematic diagram of a fluorescence image of a cell where no membrane translocation reaction has occurred.
Figure 2B:
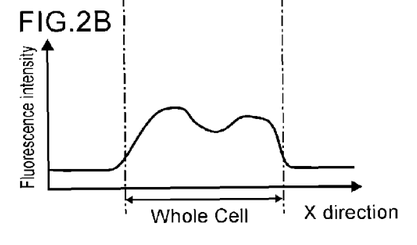
FIG. 2B shows a fluorescence intensity distribution on a horizontal line in FIG. 2A.
Figure 2C:
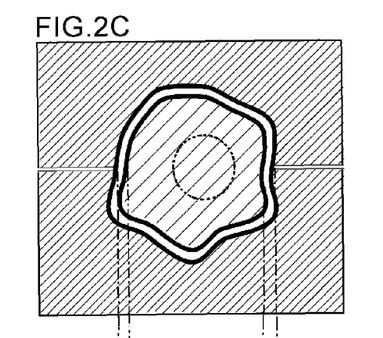
FIG. 2C is a schematic diagram of a fluorescence image of a cell where a membrane translocation reaction has occurred.
Figure 2D:
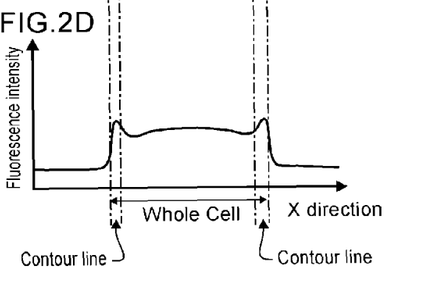
FIG. 2D shows a fluorescence intensity distribution on a horizontal line in FIG. 2C.
Figure 2E:
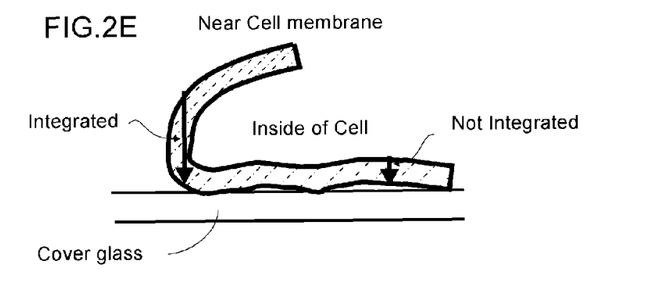
FIG. 2E is a typical sectional diagram of a cell in which the membrane translocation reaction occurred so that the fluorescently labeled protein (gray region) accumulate on the cell membrane, where it is explained that the periphery of the cell image looks bright when the fluorescent labels accumulate near the cell membrane.

FIGS. 2A-2E schematically fluorescence images before and after a membrane translocation reaction of one certain cell with fluorescently labeled translocation molecules (In this regard, the cell is an adhesive cell in the condition where it stuck to the bottom surface of a well of a micro titer plate.). Referring to the drawing, in the cell before a membrane translocation reaction (FIG. 2A), the translocation molecules exist in a liberated form all over the cytoplasm so that the fluorescence intensity distribution in the cell is represented as in the form shown in FIG. 2B. In this cell, when a certain specific stimulus is applied and a membrane translocation reaction occurs, the translocation molecules accumulate near the cell membrane so that, in the fluorescence image, the fluorescence intensity of the periphery of the cell increases relatively as shown in FIGS. 2C and 2D (In practical, although the translocation molecules accumulates on the whole surface of the cell including the upper and lower sides of the cell, the fluorescence intensity in a fluorescence image is integrated in the direction of the focal depth of the objective as shown in FIG. 2E, and therefore the fluorescence intensity of only the perimeter of the cell increases in the fluorescence image.).

When the change of distribution of the fluorescence intensity occurs owing to the membrane translocation reaction, in the past, an observer or an experimenter has compared FIG. 2A with FIG. 2C or 2C or 2D, and whether or not there was any change of distribution of the fluorescence intensity owing to the membrane translocation reaction is judged, so to speak, sensuously, and therefore the criterion of the judgment varies, and also, it was time consuming because a judgment has been made for each cell. Then, in the present invention, a region occupied by a cell in a fluorescence image is defined based on brightness (fluorescence intensity) in the fluorescence image; a contour line of a predetermined width is determined; and whether or not a membrane translocation reaction occurred is numerically determined based on the ratio of the brightness on the contour line and the brightness in the inside of the contour line (refer to FIG. 2D). In this regard, the judgment of a membrane translocation reaction based on the ratio of the brightness on the contour line and the brightness in the inside of the contour line, preferably, is carried out in accordance with whether or not the ratio of the average of the brightness on the whole contour line region and the average of the brightness in the whole region in the inside of the contour line exceeds a predetermined value. It should be understood that these processes are automatically carried out in the image analysis apparatus 100 by computation using the brightness values and the coordinate values of individual pixels in an image data so that the result will not be influenced by any variation in the criterion of the judgment, and also that the time and burden required of an observer or an experimenter will be largely reduced.

Preparation of a Cell Sample

As already noted in the column of "Summary of Invention", the above-mentioned inventive apparatus or method of the judging of a membrane translocation reaction enables the judgment of a reaction that proteins which has been liberated into cytoplasm of a cell accumulate on a cell membrane of the cell owing to the applying of a stimulus to the cell, or a reaction that proteins present in organelles in a cell accumulate on a cell membrane of the cell owing to the applying of a stimulus to the cell. For instance, it is possible to conduct the judgment of the reaction of the moving of protein kinase C (PKC), floating in cytoplasm in a Hela cell, a kind of a cervical cancer cell strain cell, to its cell membrane owing to a stimulus of PMA (Phorbol Myristate Acetate) or radiation (an example of a membrane translocation reaction from cytoplasm to a cell membrane), or the reaction of the rapid moving of GLUT4 in fat cell strain 3T3-L1, a molecule present on Trans Golgi membrane under the absence of insulin, to the cell membrane surface in response to stimulation with insulin (an example of a membrane translocation reaction from a membrane of an organelle to a cell membrane. In this respect, by this reaction, GLUT4 will exhibit an activity of taking glucose into a cell.).

In the cells for the judgment of the presence or absence of a membrane translocation reaction in the present invention, their internal translocation molecules should be fluorescently labeled. Preferably, the introduction of a fluorescent label to a cell is carried out by making a cell express translocation molecules while fusing with a fluorescent protein or a halo tag molecule through gene introduction technique. In a case of making cells express translocation molecules into which a halo tag molecule is introduced, after the expression, the fluorescent labeling of the translocation molecules is conducted by introducing a fluorescent dye capable of binding specifically to the tag molecule into the cells. This introduction of the fluorescent label to the cell may be conducted by an arbitrary method well-known for a person skilled in the art.

For instance, in the judging of a membrane translocation reaction of PKC owing to a stimulus of PMA in a HeLa cell, a kind of a cervical cancer cell strain cell, first, DNA vectors of PKC into which a halo tag molecule is introduced is introduced to cells using an arbitrary lipofection gene introduction technique. Then, the cells are cultured for 16 to 24 hours, and washed appropriately, and a fluorescent dye, TMR (tetramethylrhodamine), with a halo tag ligand is added thereto. TMR with a halo tag ligand automatically invades into the cells, and specifically binds to the halo tag of PKC molecule having been expressed within the cells. Then, 15 minutes after, the cells are appropriately washed for the removal of the fluorescent dye from the culture solution; a culture medium is further added thereto; then, PMA is given to the culture medium, which is left at rest for around 10 minutes. Here, when the introduction of DNA has been successfully done, the TMR-labeled PKC molecules move from cytoplasm to a cell membrane in accordance with the response of the HeLa cell to the stimulus of PMA, and thereby the fluorescence intensity of the periphery of a cell image increases as schematically shown in FIG. 2C. In this regard, the accumulation of the above-mentioned PKC molecules near the cell membrane disappears relatively quickly, and thus, in the observation, it is preferable to add 80% of ethanol to the culture medium to fix the cell in the condition where the membrane translocation reaction occurred.

As well known for a person skilled in the art, PKC, used here, reversibly controls functions of various proteins through phosphorylation and dephosphorylation in the process of intracellular signal information transmission to adjust various cellular functions, while deeply participating in intracellular mechanisms related to cellular proliferation, specialization, canceration, and apotosis. Accordingly, the above-mentioned judgment of a membrane translocation reaction of PKC conducted according to the present invention is expected to be used as tools for search of an intracellular signal transmitter molecule, screening of substances having arbitrary physiological activities and evaluation of gene introduction efficiency.

Further, in the judging of a membrane translocation reaction of GLUT4 from Torrance Golgi membrane to a cell membrane surface owing to an insulin stimulus in fat cell strain 3T3-L1, a fluorescent protein-fused GLUT4 is made expressed by introducing a gene which expresses GLUT4 fusing with a fluorescent protein, such as GFP, into the fat cell strain by means of a gene introduction technique as in the case of Hela cells. If the gene introduction has been successfully done, fluorescent protein-fused GLUT4 will move to near the cell membrane on insulin stimulation to these cells by a method arbitrary for a person skilled in the art, and thereby the fluorescence intensity of the periphery of a cell image will increase as schematically shown in FIG. 2C.

The sample to be laid on the stage of a fluorescence microscope may be prepared by dispensation of the cell sample prepared as described above into wells of a micro plate P or by the fluorescent labeling and the application of a stimulus through the above-mentioned processes after dispensation of cells into the well of a micro plate P. In this regard, as already mentioned, the brightness on the contour line of a cell is liable to change in accordance with the focal position of the objective, and thus, a sample to which the focus of the objective is easily to adjust is more advantageous. So, preferably, cells may be arbitrary adhesive cells that adhere on the bottom surface of wells of a micro plate P. However, it should be understood that cells may be globular or not stick to the bottom surface of a well (In that case, preferably, they are fixed by an arbitrary method for making them stick to the bottom surface of a well of a micro plate P.).

Figure 3A:
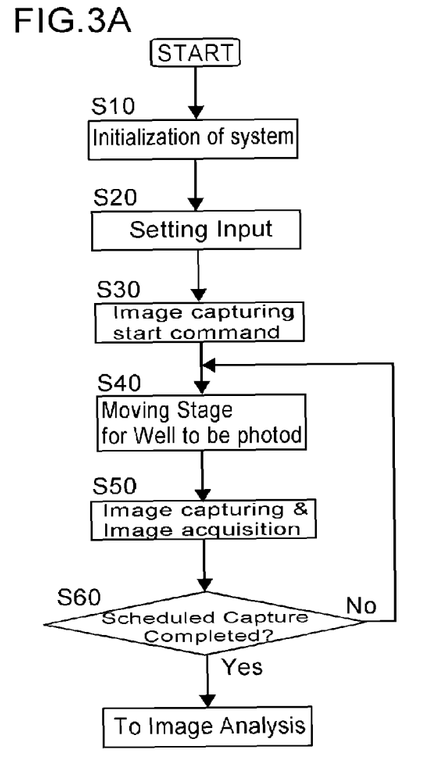
FIG. 3A is a drawing, in the form of a flow chart, of the process of acquiring a fluorescence image of a cell sample using the system of FIG. 1.

Acquisition of a Fluorescence Image of a Cell Using the Fluorescence Microscope Observation System FIG. 3A shows the processes until the acquisition of a fluorescence image of a cell sample P prepared as described above as image data in the above-mentioned fluorescence microscope observation system in the form of a flow chart. Referring to the drawing, first, when an observer or an experimenter switches on the power of the image analysis apparatus 100 (and multi-controller) and operates the keyboard 102 in the image analysis apparatus 100 to start specialized software, the initialization of the setting of each part of the fluorescence microscope 1 is executed, and, on the monitor, an image for commanding various settings and operations of the fluorescence microscope observation system is displayed (Step 10). In this step, from the image analysis apparatus 100, the observer or experimenter inputs various settings, such as wells to be photographed in the micro titer plate P to which the cell sample prepared as described above was dispensed, the number of photographs for one well, excitation light wavelength, etc.(Step 20). Also, at this time, the height of the objective to be maintained with the autofocus unit may be determined for determining the interval between the objective 4 and the bottom surface of the micro titer plate P so that the focus of the objective 4 will be adjusted to the arbitrary cell samples in wells. Further, the compensation ring 6 of the objective 4 may also be automatically adjusted to be fit to the thickness of the cover glass at the bottom surface of the micro titer plate P.

Then, when the observer or experimenter gives an image capturing start command from the image analysis apparatus 100, the excitation light source 6 is lighted up (or a shutter, not illustrated, of the optical path of the excitation light source 6 is opened) and the camera 16 is operated to start the capturing of fluorescence images (Step 30). In the capturing of fluorescence images, first, the electrically driven stage 2 is moved in the XY directions under control of the multi-controller 10 for making a well to be photographed, inputted in Step 20, fall into the field of view of the objective 4 (Step 40). In this movement of the stage, as already mentioned, the relative positions of the focus of the objective 4 to the bottom surface of the well is maintained constant by the autofocus unit, and therefore, basically, it is unnecessary for the observer or experimenter to conduct the adjustment of the height of the objective. Then, when the movement of the well is completed, the fluorescence image formed on the light receiving surface of the camera is taken through the multi-controller 10 into the image analysis apparatus 100 as image data (a still picture) (Step 50). In this regard, as understood for a person skilled in the art, it should be understood that the acquisition of image data is performed in a manner suited for the type of the camera to be used. For instance, for a CCD camera of the type that outputs images at a video rate, etc., images of the arbitrarily set-up number of frames may be integrated and acquired as an image data. Further, for a cooled CCD, an image corresponding to electrical charge accumulated on the light receiving surface for an exposure time set up arbitrarily is taken into the image analysis apparatus 100 as one image data. Then, when the capturing of the fluorescence image for the present well is completed, the stage is moved and the capturing of the fluorescence image of the following well is performed (Steps 40 and 50). Consequently, when the acquisitions of the image data of the fluorescence images for all the scheduled wells are completed (Step 60), the analysis of image data as described below is performed.

Procedures for Judgment of a Membrane Translocation Reaction

Figure 3B:
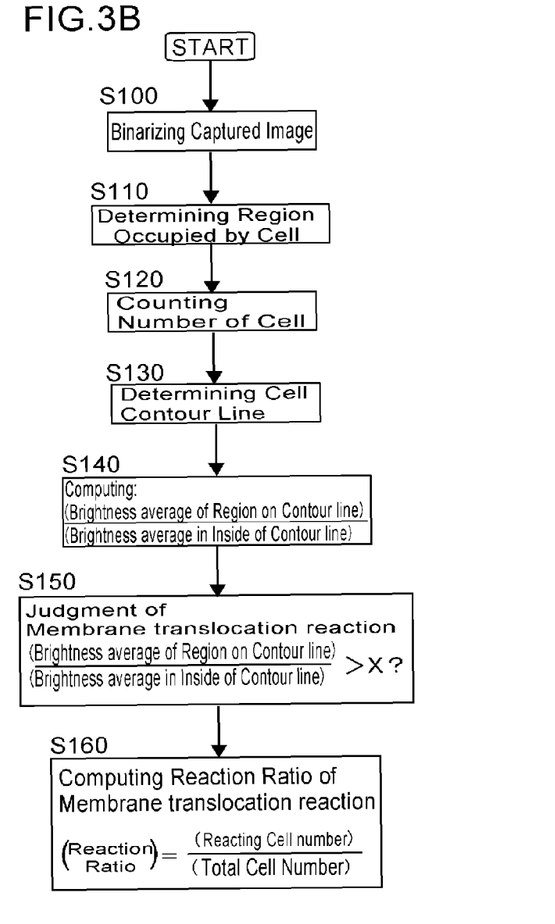
FIG. 3B is a drawing, in the form of a flow chart, of the process of the judging of a membrane translocation reaction from a fluorescence image obtained by the process in FIG. 3A.
Figure 4A:
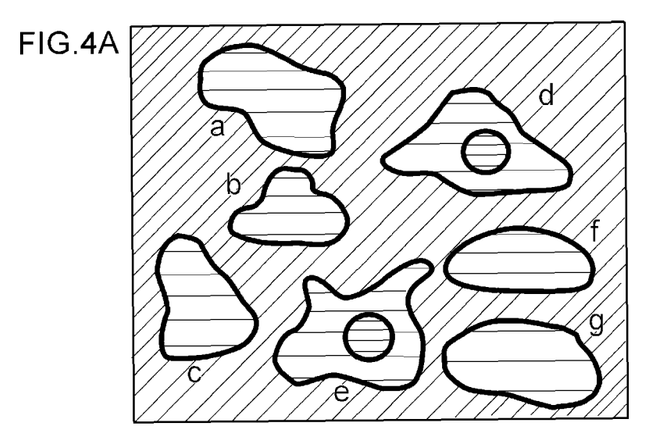
FIG. 4A is a schematic diagram of a fluorescence image of a cell sample after stimulation. In the drawing, cells a-c, f and g are in the condition that a membrane translocation reaction has occurred, and cells d and e are in the condition that no membrane translocation reaction has occurred.

FIG. 3B shows the processes for carrying out the judgment of a membrane translocation reaction from the fluorescence images (FIG. 4A) of the cell sample obtained in FIG. 3A in the form of a flow chart. In this connection, although the image analysis explained below is performed subsequently after the capturing of fluorescence images, it may be conducted through taking into the image analysis apparatus 100 the image data which was prepared by, and stored into, a different apparatus or system.

Referring to the drawing, first, based on the fluorescence intensity in the fluorescence image including the images of a plurality of cells, regions occupied by the images of cells are determined (Steps 100 and 110). As understood from FIGS. 2A-2E, since the fluorescence intensity of a region occupied by a cell is higher than the background, it is possible to consider that a cell is present on a region of pixels having the fluorescence intensity more than a certain threshold. In more detail, since the distribution of a fluorescence intensity spreads a little wider than a region on which a cell is present exactly, it can be considered that a cell lies on a region of pixels having the fluorescence intensity more than a predetermined threshold which is arbitrarily set to the skirt of the fluorescence intensity distribution. In the computation process, typically, the fluorescence image is binarized with a predetermined threshold (the brightness of 1 is given to the pixels having the brightness more than the threshold and the brightness of 0 is given to the pixels having the brightness lower than the threshold. Step 100, FIG. 4B), and then, the region having been given the brightness 1 and spreading out continuously beyond a predetermined area (number of pixels) in the XY directions of the image is determined as a region occupied by a cell (Step 110). The coordinates of the regions occupied by the cells as determined above are recorded for individual cells, and are used for the following computation.

In this connection, the algorithm of detection of a region having been given the brightness 1 and spreading out continuously beyond a predetermined area (number of pixels) may be arbitrarily designed by a person skilled in the art. When a region of brightness 0 is present in the interior of a region where pixels of brightness 1 spread out continuously to an area more than a predetermined area due to a nucleus or other organelle being not fluorescently labeled as in the cell images d and e in FIG. 4B, this interior pixel region of brightness 0 is also defined as a region occupied by a cell.

When the above-mentioned regions occupied by the cells are determined, the number of the regions will be used for the following computation as the number of the cells in the fluorescence image (Step 120).

After the defining of the region occupied by each cell and the counting of the number of the cells were done as described above, further, in each of the pixel regions occupied by the individual cell images, a contour line having a predetermined width from the periphery of the region toward its interior is specified with the coordinates on image data (Step 130). In this regard, the width of the contour line may be arbitrarily set up by an observer or an experimenter. As already described in the column of "Summary of invention", the extent of spreading of the fluorescence intensity near the cell periphery in a membrane translocation reaction may vary depending upon the kinds of cells. As understood from FIG. 2C, if the width of the contour line is too wider than the spread of the increase portion of the fluorescence of the outer periphery of a cell image, the region where the fluorescence increase is not seen would enter into the contour line so that the change of the fluorescence intensity on the contour line would be reduced. To the contrary, if the width of the contour line is too narrower than the spread of the increase portion of the fluorescence of the outer periphery of a cell image, the number of pixels whose brightness value is to be picked up would be reduced, leading to the reduction of the reliability of a result, and also the contour line would become offset from the portion whose fluorescence greatly increased, where the change of the fluorescence intensity on the contour line would also be reduced. In order to set up a suitable width of a contour line, it is necessary to conduct a preliminary experiment to determine the suitable width.

Figure 4B:
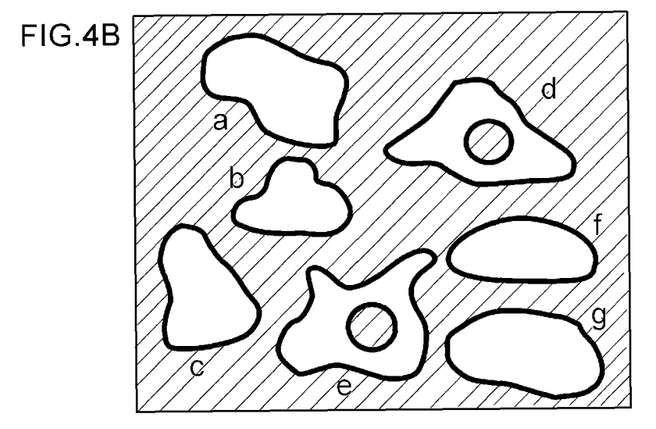
FIG. 4B is an image obtained by binarizing the image of FIG. 4A at a predetermined threshold.
Figure 4C:
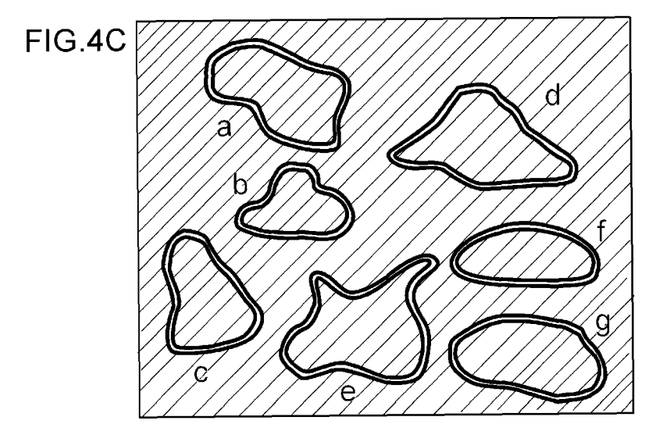
FIG. 4C is an image showing the positions of contour lines.

In the binarized image of FIG. 4B, when the brightness 1 is given to a thinner region with a width of several pixels from the periphery of a cell image inwardly of the region, i.e., the pixels on a contour line, and the brightness 0 is given to the pixels in the inside of the contour line, there will be formed an image consisting only of the contour line as shown in FIG. 4C.

After the pixel regions occupied by the individual cells and the regions on the contour lines were defined in the above-mentioned way, for each cell, the brightness values of the pixels of the region on the contour line are obtained from the image data of the fluorescence image; their average is computed; and further, the brightness values of the pixels in the inside of the region on the contour line of the pixel region occupied by the cell are obtained from the image data of the fluorescence image; and their average is computed. And, the ratio of the brightness average of the region on the contour line to the brightness average of the inside of the contour line is computed for each cell (Step 140). As already described, since the coordinates of the pixel regions occupied by the cells and the regions on the contour lines have been determined, this computation is automatically performed by an arbitrary program in the image analysis apparatus constructed with a computer. Thus, when > (The brightness average of the region on the contour line)/(the brightness average in the inside of the contour line)>$X$ is established, it is judged that translocation molecules have accumulated near a cell membrane and a membrane translocation reaction has occurred (Step 150). In this regard, the predetermined value X may be previously set up by the observer or experimenter. Moreover, in the above-mentioned judgment of a membrane translocation reaction, the evaluation of the high and low of the ratio of the brightness averages may be done with plural different values, whereby the degree of the progress of a membrane translocation reaction may be classified into several stages. Since the predetermined value X is used while being fixed for at least all the currently inspected cells, any variation in the judgment criterion will be avoided.

Moreover, after the judgment of the presence or absence of occurrence of the membrane translocation reaction of each cell, it may be conducted to count the number of cells producing the membrane translocation reaction and to compute, with the previously counted total number of the cells, the reaction ratio of the membrane translocation reaction by > (The number of cells producing the membrane translocation reaction)/(the total number of the cells)

(Step 160).

By the way, prior to the above-mentioned series of image processing, preferably, the shading correction and background correction may be executed for the image data of fluorescence images in a well-known manner. Further, the total number of cells may be determined by capturing a fluorescence image consisting of nuclei stained with a different dye; binarizing the image; and counting the number of the regions occupied by the individual nuclei. Since the nuclear shapes and sizes are stable, the region occupied by a nucleus in each cell can be easily and more certainly determined, and therefore the counting of the number of cells is possible with sufficient accuracy even when images of cells overlap on one another.

The invention claimed is:

1. A cell image analysis apparatus for judging a presence or an absence of a membrane translocation reaction occurring in a cell owing to application of an arbitrary stimulus to the cell, characterized by comprising:
   a means that acquires as an image data a fluorescence microscopic image of a cell after the application of the stimulus in which cell translocation molecules moving to a cell membrane in the membrane translocation reaction have been fluorescently labeled;
   a means that determines a region occupied by the cell in the image data of the fluorescence microscopic image of the cell;
   a means that determines a contour line of the cell which has a width of a predetermined number of pixels from a periphery of the region occupied by the cell; and
   a means that judges the presence or absence of the membrane translocation reaction based on a brightness value on the contour line of the cell and a brightness value in an inside of the contour line of the cell in the image data of the fluorescence microscopic image of the cell.

2. An apparatus of claim 1, characterized in that the means that judges the presence or absence of the membrane translocation reaction computes an average of brightness values of all pixels on the contour line of the cell and an average of brightness values of pixels in the inside of the contour line of the cell and judges that the membrane translocation reaction occurred when a ratio of the average on the contour line of the cell to the average in the inside of the contour line of the cell exceeds a predetermined value.

3. An apparatus of claim 1, characterized in that the fluorescence microscopic image includes fluorescence microscopic images of a plurality of cells; the means that determines the region occupied by the cell determines a region occupied by each of the plurality of cells; the means that determines the contour line of the cell determines a contour line of each of the plurality of cells; and the means that judge the presence or absence of the membrane translocation reaction judges the presence or absence of the membrane translocation reaction based on a brightness value on the contour line and a brightness value in the inside of the contour line for each of the plurality of cells.

4. An apparatus of claim 3, characterized by comprising a means that counts the number of the plurality of cells in the fluorescence microscopic image based on the regions occupied by the cells.

5. An apparatus of claim 4, further characterized by computing a ratio of the number of the cells where the membrane translocation reaction occurred in the plurality of cells in the fluorescence microscopic image.

6. An apparatus of claim 1, characterized in that the predetermined width of the contour line determined by the means that determines the contour line of the cell can be set up by a user.

7. An apparatus of claim 1, characterized in that the cell is a cell which adheres on a bottom surface or a upper surface of an observation sample container put in a fluorescence microscope for obtaining the fluorescence microscopic image of the cell; and the apparatus further comprises a means that controls a position of an objective of the fluorescence microscope to adjust a focus of the objective to the cell by adjusting automatically the focus of the objective to the bottom surface or the upper surface of the observation sample.

8. A computer program for cell image analysis for judging a presence or an absence of a membrane translocation reaction occurring in a cell owing to application of an arbitrary stimulus to the cell, characterized by making a computer execute procedures of:
   acquiring as an image data a fluorescence microscopic image of a cell after the application of the stimulus in which cell translocation molecules moving to a cell membrane in the membrane translocation reaction have been fluorescently labeled;
   determining a region occupied by the cell in the image data of the fluorescence microscopic image of the cell;
   determining a contour line of the cell which has a width of a predetermined number of pixels from a periphery of the region occupied by the cell; and
   judging the presence or absence of the membrane translocation reaction based on a brightness value on the contour line of the cell and a brightness value in an inside of the contour line of the cell in the image data of the fluorescence microscopic image of the cell.

9. A computer program of claim 8, characterized in that an average of brightness values of all pixels on the contour line of the cell and an average of brightness values of pixels in the inside of the contour line of the cell are computed and it is judged that the membrane translocation reaction occurred when a ratio of the average on the contour line of the cell to the average in the inside of the contour line of the cell exceeds a predetermined value in the procedure of judging the presence or absence of the membrane translocation reaction.

10. A computer program of claim 8, characterized in that the fluorescence microscopic image includes fluorescence microscopic images of a plurality of cells; a region occupied by each of the plurality of cells is determined in the procedure of determining the region occupied by the cell; a contour line of each of the plurality of cells is determined in the procedure of determining the contour line of the cell; and the presence or absence of the membrane translocation reaction is judged based on a brightness value on the contour line and a brightness value in the inside of the contour line for each of the plurality of cells in the procedures of judging the presence or absence of the membrane translocation reaction.

11. A computer program of claim 10, characterized in that the number of the plurality of cells in the fluorescence microscopic image is counted based on the regions occupied by the cells and a ratio of the number of the cells where the membrane translocation reaction occurred in the plurality of cells in the fluorescence microscopic image is computed.

12. A method for judging a presence or an absence of a membrane translocation reaction occurring in a cell owing to application of an arbitrary stimulus to the cell, characterized by comprising steps of:
   acquiring as an image data a fluorescence microscopic image of a cell after the application of the stimulus in which cell translocation molecules moving to a cell membrane in the membrane translocation reaction have been fluorescently labeled;
   determining a region occupied by the cell in the image data of the fluorescence microscopic image of the cell;
   determining a contour line of the cell which has a width of a predetermined number of pixels from a periphery of the region occupied by the cell; and
   judging the presence or absence of the membrane translocation reaction based on a brightness value on the contour line of the cell and a brightness value in an inside of the contour line of the cell in the image data of the fluorescence microscopic image of the cell.

13. A method of claim 12, characterized in that, in the step of judging the presence or absence of the membrane translocation reaction, an average of brightness values of all pixels on the contour line of the cell and an average of brightness values of pixels in an inside of the contour line of the cell are computed; and it is judged that the membrane translocation reaction occurred when a ratio of the average on the contour line of the cell to the average in the inside of the contour line of the cell exceeds a predetermined value.

14. A method of claim 12, characterized in that the fluorescence microscopic image includes fluorescence microscopic images of a plurality of cells; a region occupied by each of the plurality of cells is determined in the step of determining a region occupied by the cell, a contour line of each of the plurality of cells is determined in the step of determining a contour line of the cell; and the presence or absence of the membrane translocation reaction is judged based on a brightness value on the contour line and a brightness value in an inside of the contour line for each of the plurality of cells in the step of judging the presence or absence of the membrane translocation reaction.

15. A method of claim 14, characterized by counting the number of the plurality of cells in the fluorescence microscopic image based on the regions occupied by the cell.

16. A method of claim 15, further characterized by computing a ratio of the number of the cells where the membrane translocation reaction occurred in the plurality of cells in the fluorescence microscopic image.

17. A method of claim 12, wherein the membrane translocation reaction to be judged is a reaction that proteins having been liberated in cytoplasm of the cell accumulate on a cell membrane of the cell when the stimulus is applied to the cell.

18. A method of claim 12, wherein the membrane translocation reaction to be judged is a reaction that proteins present in an organelle in the cell accumulate on a cell membrane of the cell when the stimulus is applied to the cell.

19. A method of claim 12, wherein the cell is an adhesive cell.

20. A method of claim 12, characterized by comprising steps of: introducing into the cell a gene for expressing a translocation molecule moving to a cell membrane in the membrane translocation reaction with fusing with a fluorescent protein; and making the translocation molecule fusing with the fluorescent protein express in the cell prior to the step of acquiring a fluorescence microscopic image of a cell.

21. A method of claim 12, characterized by comprising steps of: introducing into the cell a gene for introducing a tag molecule into a translocation molecule moving to a cell membrane in the membrane translocation reaction; making the translocation molecule into which the tag molecule was introduced express in the cell; and introducing into the cell a fluorescent dye binding specifically to the tag molecule to fluorescently label the translocation molecule prior to the step of acquiring a fluorescence microscopic image of a cell.

* * * * *